100
United States Patent [19]

Stahly

[11] Patent Number: 4,935,514

[45] Date of Patent: Jun. 19, 1990

[54] THIATION PROCESS

[75] Inventor: Barbara C. Stahly, Baton Rouge, La.

[73] Assignee: Ethyl Corporation, Richmond, Va.

[21] Appl. No.: 362,050

[22] Filed: Jun. 6, 1989

[51] Int. Cl.$^5$ ............................................ C07D 267/14
[52] U.S. Cl. .................................... 540/490; 540/488;
558/23; 560/9; 560/147; 564/74; 564/78;
568/20
[58] Field of Search .................. 540/488, 490; 558/23;
560/9, 147; 564/74, 78; 568/20

[56] References Cited

U.S. PATENT DOCUMENTS 4,439,617 3/1984 Sestanj et al. ......................... 560/39
4,592,866 6/1986 Cale ...................................... 540/490
4,663,452 5/1987 Lilje .................................... 540/490

FOREIGN PATENT DOCUMENTS 741109 11/1943 Fed. Rep. of Germany ........ 564/74

OTHER PUBLICATIONS

Scheeren et al., "Synthesis" (1973) pp. 149–151.

Primary Examiner—Robert T. Bond
Attorney, Agent, or Firm—Patricia J. Hogan

[57] ABSTRACT

An amide is thiated to the corresponding thioamide by reacting it with phosphorus pentasulfide in the presence of an adjuvant selected from diatomaceous earth, zeolites, and molecular sieves.

16 Claims, No Drawings

THIATION PROCESS

FIELD OF INVENTION

This invention relates to thioamides and more particularly to a process for preparing such compounds by the thiation of the corresponding amides.

BACKGROUND

As disclosed in U.S. Pat. Nos. 4,439,617 (Sestanj et al.), 4,592,866 (Cale), and 4,663,452 (Lilje), German Patent No. 741,109 (Dieterle), and Scheeren et al., *Synthesis*, 1973, pp. 149–151, it is known that carbonyl compounds can be converted to the corresponding thiono compounds by reaction with tetraphosphorus decasulfide (more commonly, though less accurately, known as phosphorus pentasulfide). Scheeren et al. teach that the reaction rates can be increased by conducting such thiations in the presence of sodium sulfide, carbonate, or bicarbonate and a polar solvent, Dieterle discloses the use of alkaline earth carbonates and oxides in such thiations to increase yields, and Lilje teaches that both the reaction rates and yields can be improved by conducting such thiations in the presence of an alkali metal bicarbonate and a hydrocarbon diluent.

SUMMARY OF INVENTION

An object of this invention is to provide a novel process for thiating amides.

Another object is to provide such a process that is capable of producing amides in higher yields and/or shorter times.

A further object is to provide such a process in which the reaction mass is easier to handle and work up.

These and other objects are attained by reacting an amide with phosphorus pentasulfide in the presence of an adjuvant selected from diatomaceous earth, zeolites, and molecular sieves.

DETAILED DESCRIPTION

The amide that is used in the practice of the invention may be any amide that is thiatable with phosphorus pentasulfide, e.g., an aliphatic, cycloaliphatic, aromatic, or heterocyclic amide. Such compounds, of course, are already known and include, e.g., imidazolone, formamide, acetamide, propionamide, phenylacetamide, N-methyl phenylacetamide, N-(3,4-dimethoxyphenyl)-acetamide, N,N-dimethylformamide, N-(p-chlorophenyl)acetamide, p-nitrobenzamide, N-phenyl-p-aminobenzamide, N-phenyl-p-dimethylaminobenzamide, saccharamide, camphorimide, methyl N-[(6-methoxy-5-trifluoromethylnaphthalenyl)carbonyl]-N-methylaminoethanoate, 2-(2-chloroethyl)-2,3-dihydro-4-methyl-1,4-benzoxazepin-5(4H)-one, 2-(2-chloroethyl)-2,3-dihydro-4-methylpyrido[3,2-f]-1,4-oxazepin-5(4H)-one, 2-(2-chloroethyl)-2,3-dihydro-4-methylnaphth[2,3-f]-1,4-oxazepin-5(4H)-one, etc.

In a preferred embodiment of the invention, the amide is an aromatic amide. In a particularly preferred embodiment, it is an alkyl or aralkyl N-[(6-alkoxy-5-trifluoromethylnaphthalenyl)-carbonyl]-N-alkylaminoethanoate wherein the alkyl groups contain 1–6 carbons, such as the amidoesters of Sestanj et al., the teachings of which are incorporated herein by reference. In another particularly preferred embodiment, the carbonyl compound is an aromatic 2,3-dihydro-1,4-oxazepin-5(4H)-one such as those taught in Cale (the teachings of which are incorporated herein by reference) and including, e.g., 2-(2-haloethyl)-2,3-dihydro-1,4-benzoxazepin-5(4H)-ones, 2-(2-haloethyl)-2,3-dihydro-4-alkylpyrido-[3,2-f]-1,4-oxazepin-5(4H)-ones, etc., especially those substituted with an alkyl or aralkyl group in the 4-position.

The phosphorus pentasulfide, as indicated above, is the thiating agent that is also known as tetraphosphorus decasulfide. It is preferably employed in substantially pure form and is used in at least the stoichiometric amount, generally in excess of that amount. There is no maximum to the amount that may be employed except for the maximum that might be set by economic considerations. Most commonly, the sulfide is used so as to provide at least one atom, preferably at least about two atoms, of sulfur per carbonyl group.

The adjuvant employed in the reaction may be diatomaceous earth, a zeolite, or a molecular sieve but is preferably diatomaceous earth. It is normally used in an amount of at least about 5%, most commonly about 60–70%, based on the weight of the amide. There is no apparent maximum to the amount that may be used.

Although the reaction may be conducted in the absence of a diluent, it is generally preferred to use a diluent. When a diluent is employed, it may be a polar diluent, such as acetonitrile, tetrahydrofuran, diglyme, diethyl ether, etc. However, it is preferably a substantially inert normally liquid hydrocarbon which may be aliphatic, cycloaliphatic, or aromatic and is more preferably a hydrocarbon having a boiling point of at least about 50° C., most commonly about 50°–150° C. Hydrocarbons having higher or lower boiling points may be used if desired. However, since the significance of the boiling point is that the reaction is most conveniently conducted at the boiling point of the diluent, the use of a lower boiling hydrocarbon generally leads to a slower reaction, and the use of a hydrocarbon having too high a boiling point could lead to decomposition of the product or a starting material.

Examples of hydrocarbons that can be used as the diluent include hexane, heptane, octane, nonane, decane, cyclopentane, cyclohexane, cycloheptane, benzene, toluene, xylene, etc., as well as less easily available liquid hydrocarbons. It is generally preferred to employ an aromatic hydrocarbon, such as toluene.

The reaction is conducted by combining the aforementioned ingredients of the reaction mixture and heating them at a suitable temperature, preferably reflux temperature, until a substantial amount of the amide has been converted to the corresponding thioamide. The time required for the reaction varies with the particular starting materials and temperature employed but is frequently about 20–30 minutes. Yields may be improved by employing anhydrous starting materials and reaction conditions.

In a preferred embodiment of the invention, the reaction is conducted by preslurrying the phosphorus pentasulfide and adjuvant in at least a portion of the diluent, then adding the amide (preferably as a solution in a portion of the diluent) with agitation, and heating the reaction mixture at reflux temperature until a substantial amount of the amide has been converted to the corresponding thioamide. It is frequently preferred to preheat the slurry of sulfide and adjuvant to a temperature close to the boiling point of the diluent for a suitable time, e.g., about 15–45 minutes, before the amide is added.

After completion of the reaction, the product may be recovered by conventional means. However, work-up is facilitated when the product is recovered by adding a demulsifier (i.e., an emulsion breaker) to the thioamide-containing reaction mixture at a temperature at which the demulsifier is liquid, subsequently adding water, and stirring for a time sufficient to achieve adequate admixture of the reaction mixture, demulsifier, and water prior to separating an organic phase and evaporating it to isolate the product. The demulsifier may be any material capable of changing the surface tension but is most suitably an alcohol, e.g., ethanol, or an ether, e.g., tetrahydrofuran, or diatomaceous earth. The best conditions for this procedure vary with the particular reaction mixture being worked up. However, in the case of an aromatic 2,3-dihydro-1,4-oxazepine-5(4H)-thione that has been prepared in toluene, it has been found that excellent results are obtained by cooling the reaction mixture to the boiling point of the demulsifier (e.g., tetrahydrofuran), adding about two parts by weight of demulsifier for each part of amide that was used initially, cooling to room temperature, adding about one part by weight of water for each part of the initial amide, and stirring for about 1-3 hours before separating out the various ingredients of the reaction mixture.

The invention is advantageous as a means of producing thioamides from amides in higher yields and/or shorter times and with more easily handled reaction masses than are achieved in known thiation processes. The products can be recovered by the use of a simple work-up procedure, and the process typically gives a crude product that is more than 90% pure.

The following examples are given to illustrate the invention and are not intended as a limitation thereof. In these examples the term "phosphorus pentasulfide" is used to denote the commercially-available reagent having the formula $P_4S_{10}$ and usually containing significant levels of $P_4S_9$, "Amide" is used to denote 2-(2-chloroethyl)-2,3-dihydro-4-methylpyrido-[3,2-f]-1,4-oxazepin-5-(4H)-one, and the "desired thioamide" refers to the thione corresponding to the Amide.

COMPARATIVE EXAMPLE

Part A

A suitable reaction vessel was charged with a mixture of 20 mL of toluene, 1.03 g 2.32 mmol) of phosphorus pentasulfide, and 1.94 g (23.1 mmol) of sodium bicarbonate, after which the mixture was stirred slowly and heated at reflux for 30 minutes. A solution of 1.77 g (7.35 mmol) of Amide in 28 mL of toluene was then added dropwise over a period of 20-30 minutes while maintaining reflux, and refluxing was continued for an additional 20 minutes. TLC analysis showed complete conversion of Amide to the desired thioamide.

Part B

The reaction mixture resulting from Part A was allowed to cool to 80° C., treated sequentially with 3.44 g of tetrahydrofuran and 1.72 g of aqueous 5% sodium carbonate solution, and stirred overnight at ambient temperature. The toluene product solution was decanted from residual solids. The solids were washed with two 5 mL portions of toluene, and the washes and product solution were combined. HPLC analysis of the resultant 50.6 g of solution indicated that it contained 2.92% by weight of the desired thioamide, i.e., 1.48 g (5.76 mmol), a 78% yield.

Part C

The residual solids from Part B were treated with 15 mL of concentrated ammonium hydroxide, stirred at ambient temperature for one hour, and extracted with two 15 mL portions of toluene. HPLC analysis of the combined toluene phases (26.0 g) showed 0.73% by weight of the desired thioamide, i.e., 0.19 g (0.74 mmol), a 10% yield. Thus, the total yield was 88%.

EXAMPLE I

Part A

The Comparative Example, Part A, was repeated except that the ingredients of the reaction mixture were 20 mL of toluene, 1.05 g (2.36 mmol) of phosphorus pentasulfide, 1.98 g of diatomaceous earth, and a solution of 1.8 g (7.5 mmol) of Amide in 29 mL of toluene.

Part B

The reaction mixture resulting from Part A was treated as in the Comparative Example, Part B, except that the amounts of tetrahydrofuran and aqueous 5% sodium carbonate solution employed were 3.52 g and 1.76 g, respectively. The product solution resulting from this primary workup scheme weighed 57.6 g and contained 2.31% by weight of the desired thioamide, i.e., 1.33 g (5.18 mmol), a 69% yield.

Part C

The residual solids from Part B were treated as in the Comparative Example, Part C. The resultant product solution weighed 23.1 g and contained 1.99% by weight of the desired thioamide, i.e., 0.46 g (1.8 mmol), a 24% yield. Thus, the total yield was 93%.

It is obvious that many variations may be made in the products and processes set forth above without departing from the spirit and scope of this invention.

What is claimed is:

1. In a process for preparing a thioamide by reacting an amide with phosphorus pentasulfide, the improvement which comprises conducting the reaction in the presence of an adjuvant selected from diatomaceous earth, zeolites, and molecular sieves.

2. The process of claim wherein the amide is an aromatic amide.

3. The process of claim 2 wherein the aromatic amide is an aromatic 2,3-dihydro-1,4-oxazepin-5(4H)-one.

4. The process of claim 3 wherein the aromatic amide is 2 is - 2-(2-chloroethyl)-2,3-dihydro-4-methyl-pyrido[3,2,f]-1,4-oxazepin-5(4H)-one.

5. The process of claim 2 wherein the aromatic amide is an N-[(6-alkoxy-5-trifluoromethylnaphthalenyl)carbonyl]-N-alkylaminoethanoate ester.

6. The process of claim 5 wherein the aromatic amide is methyl N-[(6-methoxy-5-trifluoromethylnaphthalenyl)carbonyl]-N-methylaminoethanoate.

7. The process of claim 1 wherein the adjuvant is diatomaceous earth.

8. The process of claim 1 wherein the reaction is conducted in a substantially inert organic diluent.

9. The process of claim 8 wherein the diluent is a substantially inert hydrocarbon having a boiling point in the range of about 50°-150° C.

10. The process of claim 9 wherein the substantially inert hydrocarbon is an aromatic hydrocarbon.

11. The process of claim 10 wherein the aromatic hydrocarbon is toluene.

12. The process of claim 8 wherein the reaction is conducted by adding a solution of the amide in a portion of the diluent to an agitated slurry of the phosphorus pentasulfide and adjuvant in the remainder of the diluent and heating the reaction mixture at reflux temperature until a substantial amount of the amide has been converted to the corresponding thioamide.

13. The process of claim 12 wherein the phosphorus pentasulfide/adjuvant slurry is heated before the amide solution is added thereto.

14. The process of claim 1 wherein the amount of adjuvant employed is at least about 5% by weight, based on the weight of the amide.

15. The process of claim 14 wherein the amount of adjuvant is about 60–70% by weight.

16. In a process for preparing 2-(2-chloroethyl)-2,3-dihydro-4-methylpyrido[3,2,f]-1,4-oxazepine-5(4H)-thione by adding a solution of 2-(2-chloroethyl)-2,3-dihydro-4-methylpyrido-[3,2,f]-1,4-oxazepin-5(4H)-one in toluene to a preheated agitated slurry of phosphorus pentasulfide and an adjuvant in toluene and heating the reaction mixture at reflux temperature, the improvement which comprises employing as the adjuvant about 60–70% by weight of diatomaceous earth, based on the weight of the starting amide.

* * * * *